United States Patent
Majumder et al.

(10) Patent No.: US 8,609,915 B2
(45) Date of Patent: Dec. 17, 2013

(54) PROCESSES FOR PREPARING ALKYLATED AROMATIC COMPOUNDS

(75) Inventors: Debarshi Majumder, Chicago, IL (US); Carl John Stevens, Lake Forest, IL (US); Robert James Schmidt, Barrington, IL (US)

(73) Assignee: UOP LLC, Des Plaines, IL (US)

( * ) Notice: Subject to any disclaimer, the term of this patent is extended or adjusted under 35 U.S.C. 154(b) by 120 days.

(21) Appl. No.: 13/418,127

(22) Filed: Mar. 12, 2012

(65) Prior Publication Data
US 2013/0237733 A1 Sep. 12, 2013

(51) Int. Cl.
*C07C 2/66* (2006.01)

(52) U.S. Cl.
USPC .......................................... 585/449; 585/467

(58) Field of Classification Search
USPC .................................................. 585/449, 467
See application file for complete search history.

(56) References Cited

U.S. PATENT DOCUMENTS

| | | | |
|---|---|---|---|
| 4,870,222 A * | 9/1989 | Bakas et al. | 585/323 |
| 4,885,412 A | 12/1989 | Pennington et al. | |
| 5,908,962 A | 6/1999 | Zakoshansky et al. | |
| 6,008,422 A | 12/1999 | Schulz et al. | |
| 6,384,153 B2 | 5/2002 | Hammer et al. | |
| 7,498,471 B2 | 3/2009 | Schultz et al. | |
| 2010/0300930 A1 | 12/2010 | Clark et al. | |
| 2011/0245558 A1 | 10/2011 | Schmidt | |

OTHER PUBLICATIONS

Barthe, P., et al., "Continuous multi-injection reactor for multipurpose production—Part I," Chemical Engineering and Technology, vol. 31, No. 8, pp. 1146-1154; Aug. 2008.

* cited by examiner

Primary Examiner — Thuan D Dang
(74) Attorney, Agent, or Firm — Mark R. Willis

(57) ABSTRACT

Processes for preparing alkylation aromatic compounds are provided herein. In an embodiment, a process for preparing alkylated aromatic compounds includes reacting an aromatic compound and an olefin in a first alkylation reaction in the presence of a first alkylation catalyst to produce a first effluent that includes an alkylated aromatic compound and unreacted aromatic compound. Unreacted aromatic compound from the first effluent and additional olefin are reacted in at least one downstream alkylation reaction in the presence of a second alkylation catalyst to produce a second effluent including the alkylated aromatic compound. A recycle stream including the alkylated aromatic compound is recycled from the second effluent to the at least one downstream alkylation reaction and, optionally, the first alkylation reaction. A ratio of the recycle stream to a total mass flow is greater in the at least one downstream alkylation reaction than in the first alkylation reaction.

12 Claims, 2 Drawing Sheets

PROCESSES FOR PREPARING ALKYLATED AROMATIC COMPOUNDS

TECHNICAL FIELD

The present invention generally relates to processes for preparing alkylated aromatic compounds and, more particularly, relates to processes for maximizing selectivity of monoalkyl aromatic compounds during preparation of alkylated aromatic compounds.

BACKGROUND

The alkylation of aromatic compounds with olefins to produce monoalkyl aromatic compounds is a well-developed process that is practiced commercially in large industrial units. One commercial application of this process is the alkylation of benzene with ethylene to produce ethylbenzene, which may subsequently be used to produce styrene. Another application is the alkylation of benzene with propylene to form cumene (isopropylbenzene), which may subsequently be used in the production of phenol and acetone. Those skilled in the art are therefore familiar with the general design and operation of such alkylation processes.

Alkylation processes generally involve alkylation of aromatic compounds with olefins in the presence of alkylation catalyst. In particular, it is known to conduct alkylation processes in a multi-bed alkylation reactor that includes at least two separate alkylation stages, with the alkylation stages each including an alkylation catalyst bed. Such multi-bed alkylation reactors can be effectively utilized to maximize yield of alkylation products. To maximize a useful life of conventional alkylation catalysts, techniques have been developed for maintaining reaction temperatures in the separate alkylation stages within a particular temperature range, with little difference in reaction temperature between the various alkylation stages. Under uncontrolled conditions, reaction temperatures tend to be highest in the first alkylation stage due higher reaction rates prevalent therein. Because less available unreacted aromatic compounds are generally present in downstream alkylation stages, reaction rates and, thus, reaction temperatures tend to be lower in downstream alkylation stages.

To enable greater temperature control in the various alkylation stages, one development that has been made is to recycle unreacted aromatic compounds from product effluent to both the first alkylation stage and to downstream alkylation stages in the alkylation reactor. For example, it is known to distill unreacted aromatic compounds from the product effluent, followed by recycling the unreacted aromatic compounds to the various alkylation stages in the alkylation reactor. In this manner, reaction rates and reaction temperatures can be controlled in the various alkylation stages. It is also known to recycle some of the reactor effluent to the various alkylation stages, without distilling the unreacted aromatic compounds, also for purposes of controlling temperatures in the various alkylation stages of the multi-bed alkylation reactors.

Despite the developments involving recycling reactor effluent and/or unreacted aromatic compounds that have been proposed to date, selectivity of monoalkyl aromatic compound formation is impacted by such developments. In particular, recycling of the reactor effluent can result in a higher incidence of dialkyl- and/or trialkyl-aromatic compound formation. The reactor effluent generally includes large quantities of monoalkyl aromatic compounds, and returning such monoalkyl compounds to the various alkylation stages risks further reaction of the monoalkyl aromatic compounds to produce the dialkyl- and/or trialkyl-aromatic compounds, thereby decreasing selectivity of monoalkyl aromatic compound formation. Further, techniques that involve distilling the unreacted aromatic compounds from the product effluent, followed by recycling the unreacted aromatic compounds to the various alkylation stages in the alkylation reactor, as described above, require significant energy expenditures to vaporize and condense the unreacted aromatic compounds. While selectivity of monoalkyl aromatic compound formation can be increased by increasing a ratio of aromatic compound to olefin, lower ratios of aromatic compound to olefin are desirable from an energy cost standpoint.

Accordingly, it is desirable to provide processes for preparing alkylated aromatic compounds that enable maximized selectivity of monoalkyl aromatic compounds to be achieved while recycling reactor effluent that includes the desirable monoalkyl aromatic compounds present therein. It is also desirable to provide such processes that enable maximized selectivity of monoalkyl aromatic compounds to be achieved without increasing a ratio of aromatic compound to olefin. Furthermore, other desirable features and characteristics of the present invention will become apparent from the subsequent detailed description of the invention and the appended claims, taken in conjunction with the accompanying drawings and this background of the invention.

BRIEF SUMMARY

Processes for preparing alkylation aromatic compounds are provided herein. In an embodiment, a process for preparing alkylated aromatic compounds includes reacting an aromatic compound and an olefin in a first alkylation reaction in the presence of a first alkylation catalyst to produce a first effluent that includes an alkylated aromatic compound and an unreacted aromatic compound. The unreacted aromatic compound from the first effluent and additional olefin are reacted in at least one downstream alkylation reaction in the presence of a second alkylation catalyst to produce a second effluent including the alkylated aromatic compound. A recycle stream including the alkylated aromatic compound is recycled from the second effluent to the at least one downstream alkylation reaction and, optionally, the first alkylation reaction. A ratio of the recycle stream to a total mass flow is greater in the at least one downstream alkylation reaction than in the first alkylation reaction.

In another embodiment, a process for preparing alkylated aromatic compounds is conducted in an alkylation apparatus that includes a multi-bed alkylation reactor. The multi-bed alkylation reactor includes a first alkylation catalyst bed and at least one downstream alkylation catalyst bed. The process includes introducing an aromatic compound and an olefin into the first alkylation catalyst bed under alkylation conditions to produce a first effluent that includes an alkylated aromatic compound and an unreacted aromatic compound. The first effluent and additional olefin are introduced into the at least one downstream alkylation catalyst bed under alkylation conditions to produce a second effluent that includes the alkylated aromatic compound. The second effluent is split into the recycle stream and a product-rich stream. The recycle stream is recycled to the at least one downstream alkylation catalyst bed and, optionally, the first alkylation catalyst bed. A ratio of the recycle stream to a total mass flow is greater in the at least one downstream alkylation catalyst bed than in the first alkylation catalyst bed.

In another embodiment, a process for preparing alkylated aromatic compounds includes reacting an aromatic compound and an olefin in a first alkylation reaction in the presence of a first alkylation catalyst to produce a first effluent that includes an alkylated aromatic compound and an unreacted aromatic compound. The unreacted aromatic compound from the first effluent and additional olefin are reacted in at least two downstream alkylation reactions in the presence of a second alkylation catalyst to produce a second effluent that includes the alkylated aromatic compound and the unreacted aromatic compound. The second effluent is split into a recycle stream and an intermediate stream. The recycle stream is recycled to the at least two downstream alkylation reactions and, optionally, the first alkylation reaction. A ratio of the recycle stream to a total mass flow is greater in the at least two downstream alkylation reactions than in the first alkylation reaction. The unreacted aromatic compound from the intermediate stream and additional olefin are reacted in at least one additional downstream alkylation reaction in the presence of a third alkylation catalyst to produce a third effluent that includes the alkylated aromatic compound. The third effluent is split into a second recycle stream and a product-rich stream, and the second recycle stream is recycled to the at least one additional downstream alkylation reaction.

BRIEF DESCRIPTION OF THE DRAWINGS

The present invention will hereinafter be described in conjunction with the following drawing figures, wherein like numerals denote like elements, and wherein.

DETAILED DESCRIPTION

Figure 1:
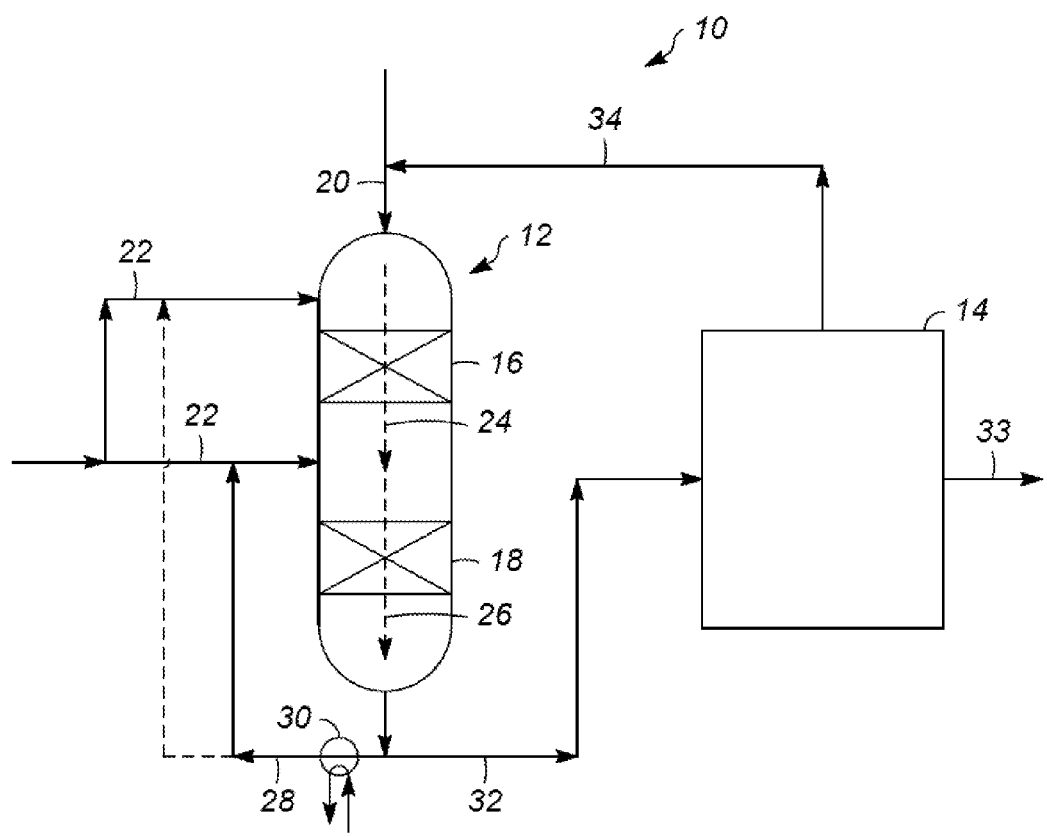
FIG. 1 is a schematic diagram of an alkylation apparatus using an exemplary embodiment of a process for preparing alkylated aromatic compounds.

The following detailed description is merely exemplary in nature and is not intended to limit the invention or the application and uses of the invention. Furthermore, there is no intention to be bound by any theory presented in the preceding background or the following detailed description.

Processes for preparing alkylated aromatic compounds are provided herein in which an aromatic compound and an olefin are reacted in a first alkylation reaction to produce a first effluent including an unreacted aromatic compound, and in which the unreacted aromatic compound from the first effluent and additional olefin are reacted in at least one downstream alkylation reaction to produce a second effluent. The processes described herein enable maximized selectivity of monoalkyl aromatic compounds to be achieved by recycling the second effluent as a recycle stream, which includes the desirable monoalkyl aromatic compounds present therein, to the at least one downstream alkylation reaction and, optionally, to the first alkylation reaction with a ratio of the recycle stream to a total mass flow being greater in the at least one downstream alkylation reaction than in the first alkylation reaction. For purposes of this disclosure, "total mass flow" refers to a total amount of all compounds that are introduced into the respective alkylation reactions including the aromatic compound, olefin (or additional olefin), and any compounds that may be present therewith when introduced into the alkylation reactions (including alkylated aromatic compounds, side-product compounds such as n-propylbenzene, non-selective heavy aromatic side products such as diphenylpropane, and the like). For purposes of this disclosure, "selectivity" means the ratio of moles of monoalkyl aromatic compounds to moles of all alkylated aromatic compounds (e.g., monoalkyl-, dialkyl-, and trialkyl-aromatic compounds) produced through the process. Because monoalkyl aromatic compounds that are introduced into the first alkylation reaction through the recycle stream are exposed to alkylation conditions in not only the first alkylation reaction but also in the at least one downstream alkylation reaction, the monoalkyl aromatic compounds are prone to further alkylation to produce multiple alkylated by-products such as dialkyl- and/or trialkyl-aromatic compounds. The multiple alkylated by-products are generally recovered and recycled in a downstream transalkylation section in order to convert such compounds back to the desired primary monoalkylated product. By establishing a lesser ratio of the recycle stream to total mass flow in the first alkylation reaction than in the at least one downstream alkylation reaction, the reintroduction of at least some of the monoalkyl aromatic compounds into the full series of alkylation reactions can be minimized, thereby decreasing the production of dialkyl- and/or trialkyl-aromatic compounds as compared to similar processes that have equal ratios of the recycle stream to total mass flow in each alkylation reaction. Further, because reaction rate in the first alkylation reaction tends to be higher than in downstream alkylation reactions, greater rates of by-product formation may be prevalent in the first alkylation reaction than in the downstream alkylation reactions such that decreasing the ratio of the recycle stream to total mass flow in the first alkylation reaction may more effectively minimize dialkyl- and/or trialkyl-aromatic compound formation than can be achieved with similar decreases in ratio of the recycle stream to total mass flow in the at least one downstream alkylation reaction. By providing a lesser ratio of the recycle stream to total mass flow in the first alkylation reaction than in the at least one downstream alkylation reaction, the processes enable the maximum selectivity of monoalkyl aromatic compounds to be achieved without increasing a ratio of aromatic compound to olefin.

An exemplary process will now be described with respect to an embodiment of an alkylation apparatus illustrated in FIG. 1. The process includes reacting the aromatic compound and the olefin in a first alkylation reaction in the presence of a first alkylation catalyst to produce a first effluent including an alkylated aromatic compound and an unreacted aromatic compound. For example, as shown in FIG. 1, an aromatic compound 20 and an olefin 22 are introduced into a first alkylation catalyst bed 16 of a multi-bed alkylation reactor 12, under alkylation conditions, to produce a first effluent 24. The first alkylation catalyst bed 16 includes a first alkylation catalyst.

The multi-bed alkylation reactor 12 includes the first alkylation catalyst bed 16 and at least one downstream alkylation catalyst bed 18, i.e., an alkylation catalyst bed that is disposed in the multi-bed alkylation reactor 12 downstream of the first alkylation catalyst bed 16. In the embodiment of FIG. 1, the multi-bed alkylation reactor 12 is shown to include one downstream alkylation catalyst bed 18. Although not shown, it is to be appreciated that in other embodiments, the alkylation apparatus may include multiple alkylation reactors having a single alkylation catalyst bed, with the alkylation reactors arranged in series.

As set forth above, the processes described herein are generally applicable to reaction of aromatic compounds and olefins in the presence of an alkylation catalyst to form an alkylated aromatic compound. Benzene is the aromatic compound of principle interest; however, it is to be appreciated that other aromatic compounds may also be used, such as alkyl-substituted benzenes, polyaromatic compounds such as naphthalene, and the like. Suitable olefins include those having from about 2 to about 20 carbon atoms, with those having from about 2 to about 4 carbon atoms being of principle interest. For example, benzene and ethylene may be reacted to form ethylbenzene as the desired monoalkyl aromatic compound. As another example, benzene and propylene may be reacted to form cumene as the desired monoalkyl aromatic compound.

Suitable alkylation catalysts that may be included in the alkylation catalyst beds 16, 18 are well known in the art, and a wide variety of alkylation catalysts can be used to catalyze the reaction of the aromatic compounds and the olefins. Examples of suitable alkylation catalysts include those characterized as aluminosilicate molecular sieves known as zeolites. Suitable zeolitic molecular sieves are crystalline aluminosilicates which, in the calcined form, may be represented by the general formula:

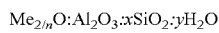

where Me is a cation, n is the valence of the cation, x has a value of from about 5 to 100, and y has a value of from about 2 to 10. Such zeolites are well-known in the art. Typical well-known zeolites that may be used include Y zeolite, beta zeolite, X zeolite, mordenite, faujasite, zeolite omega, UZM-8, ZSM-5, PSH-3, MCM-22, MCM-36, MCM-49, and MCM-56. The zeolite catalyst will usually be used in combination with a refractory inorganic oxide binder. Examples of inorganic oxide binders include silica and alumina such as, but not limited to, gamma-alumina, eta-alumina, and mixtures thereof.

The aromatic compound reacted in the first alkylation reaction generally includes fresh aromatic compounds, and may also include aromatic compounds that are provided in a recycle stream that is recycled to the first alkylation reaction as described in further detail below. "Fresh" aromatic compounds refer to aromatic compounds that are provided from source streams that have not yet passed through the alkylation reaction or that have been separated from reactor effluent from the alkylation reaction. The first alkylation reaction can be conducted over a broad range of operating conditions, depending upon the particular aromatic compounds and olefins reacted. As one specific example, when producing cumene, the aromatic compound is benzene and the olefin is propylene. The first alkylation reaction may be conducted to obtain an essentially complete conversion of the propylene to cumene, diisopropylbenzene, or heavier polyisopropylbenzenes, with cumene present in greater amounts than other reaction products. Propylene conversion is generally more than 99% and preferably more than 99.9%. To attain such high propylene conversion, a stoichiometric excess of benzene over propylene is generally present during the first alkylation reaction. For example, the molar ratio of benzene per propylene is generally from about 20:1 to 1:1, such as from about 5:1 to 1:1, in each alkylation reaction. Temperatures usually range from about 80 to about 327° C., such as from about 110 to about 204° C., in each alkylation reaction. Pressures can also vary within a wide range of from about 1 to about 130 atmospheres (atm). Because the alkylation reactions are generally conducted under liquid phase conditions, the pressure should be sufficient to maintain the benzene at least partially in a liquid phase and may fall in a range of from 15 to 50 atm. The benzene liquid hourly space velocity (LHSV) is generally from about 0.1 to about 50 hr$^{-1}$, such as from about 0.5 to about 10 hr$^{-1}$. The propylene concentration in the first alkylation reaction is generally less than about 10 mol %, such as less than about 3 mol %.

The process continues with the reaction of unreacted aromatic compound from the first effluent and additional olefin in at least one downstream alkylation reaction in the presence of a second alkylation catalyst, which can be the same as or different from the first alkylation catalyst, to produce a second effluent that includes the alkylated aromatic compound. For example, as shown in FIG. 1, the first effluent 24 and additional olefin 22 are introduced into the at least one downstream alkylation catalyst bed 18, which includes a second alkylation catalyst, under alkylation conditions to produce a second effluent 26 that includes the alkylated aromatic compound. "Additional" olefin refers to olefin that is separately introduced into the at least one downstream alkylation reaction and that is not present during the first alkylation reaction. The unreacted aromatic compound from the first effluent and additional olefin may be reacted in at least two downstream alkylation reactions, such as from 2 to about 10 additional downstream reactions, to produce the second effluent. When producing cumene, additional propylene can be introduced into each downstream alkylation reaction to make up for propylene consumed in the immediately prior alkylation reaction. The aromatic component and olefin are reacted with a temperature rise between alkylation reactions that may be less than or equal to about 50° C., such as less than or equal to about 15° C., which can be controlled through recycling a recycle stream into the various alkylation reactions as described below.

As alluded to above, the recycle stream including the alkylated aromatic compound from the second effluent is recycled to the at least one downstream alkylation reaction and, optionally, the first alkylation reaction. For example, as shown in FIG. 1, the second effluent 26 is split into the recycle stream 28 and a product-rich stream 32, and the recycle stream 28 is recycled to the at least one downstream alkylation catalyst bed 18 and, optionally, to the first alkylation catalyst bed 16. The recycle stream can be recycled to each downstream alkylation reaction or, alternatively, may only be recycled to one downstream alkylation reaction. Because the recycle stream may be employed to control temperature in the first alkylation reaction and/or at least one downstream alkylation reaction, the recycle stream may be cooled prior to recycling to the at least one downstream alkylation reaction and, optionally, the first alkylation reaction, such as through use of a heat exchanger 30 or other cooling device as shown in FIG. 1.

A ratio of the recycle stream to total mass flow, measured by weight, is greater in the at least one downstream alkylation reaction than in the first alkylation reaction, which enables maximized selectivity for production of monoalkyl aromatic compounds to be achieved. The ratio of the recycle stream to total mass flow may be greater for each downstream alkylation reaction than in the first alkylation reaction, or may be greater in only one downstream alkylation reaction. In an embodiment, a ratio of the recycle stream to total mass flow is at least 2 times greater, such as from about 2 to about 100 times greater, in the at least one downstream alkylation reaction than in the first alkylation reaction, which may apply to each of the downstream alkylation reactions or may only apply to one of the downstream alkylation reactions. In regards to actual ratios of the recycle stream to total mass flow, in an embodiment, a ratio of the recycle stream to total mass flow in the first alkylation reaction is less than or equal to about 0.5:1, such as less than or equal to about 0.01:1. In this embodiment, a ratio of the recycle stream to total mass flow in the at least one downstream alkylation reaction is greater than or equal to about 1:1, such as from about 1:1 to about 100:1. It is to be appreciated that in an embodiment, the aromatic compound and the olefin are reacted in the first alkylation reaction in the absence of the recycle stream. In particular, as shown in FIG. 1, recycle of the recycle stream 28 to the first alkylation catalyst bed 16 can be terminated such that the aromatic compound 20 and olefin 22 are introduced into the first alkylation catalyst bed 16 in the absence of the recycle stream 28.

In an embodiment, the product-rich stream is separated to recover the alkylated aromatic compound therefrom, and also to recover the unreacted aromatic compound therefrom. For example, as shown in FIG. 1, the product-rich stream 32 is separated in a separating system 14 to produce the alkylated aromatic compound 33 and a return stream 34. Separation techniques are well known in the art and may include subjecting the product-rich stream to fractionation to separate compounds of different volatilities and, optionally, transalkylation to recover by-products of the alkylation reactions, including multiple alkylated by-products. For example, the separating system 14 may include a transalkylation reactor (not shown) and one or more fractionation columns (not shown) for separating alkylated aromatic compounds of different volatilities. The unreacted aromatic compound that is recovered by the separating system 14 may be returned in the return stream 34 to the multi-bed alkylation reactor 12.

Figure 2:
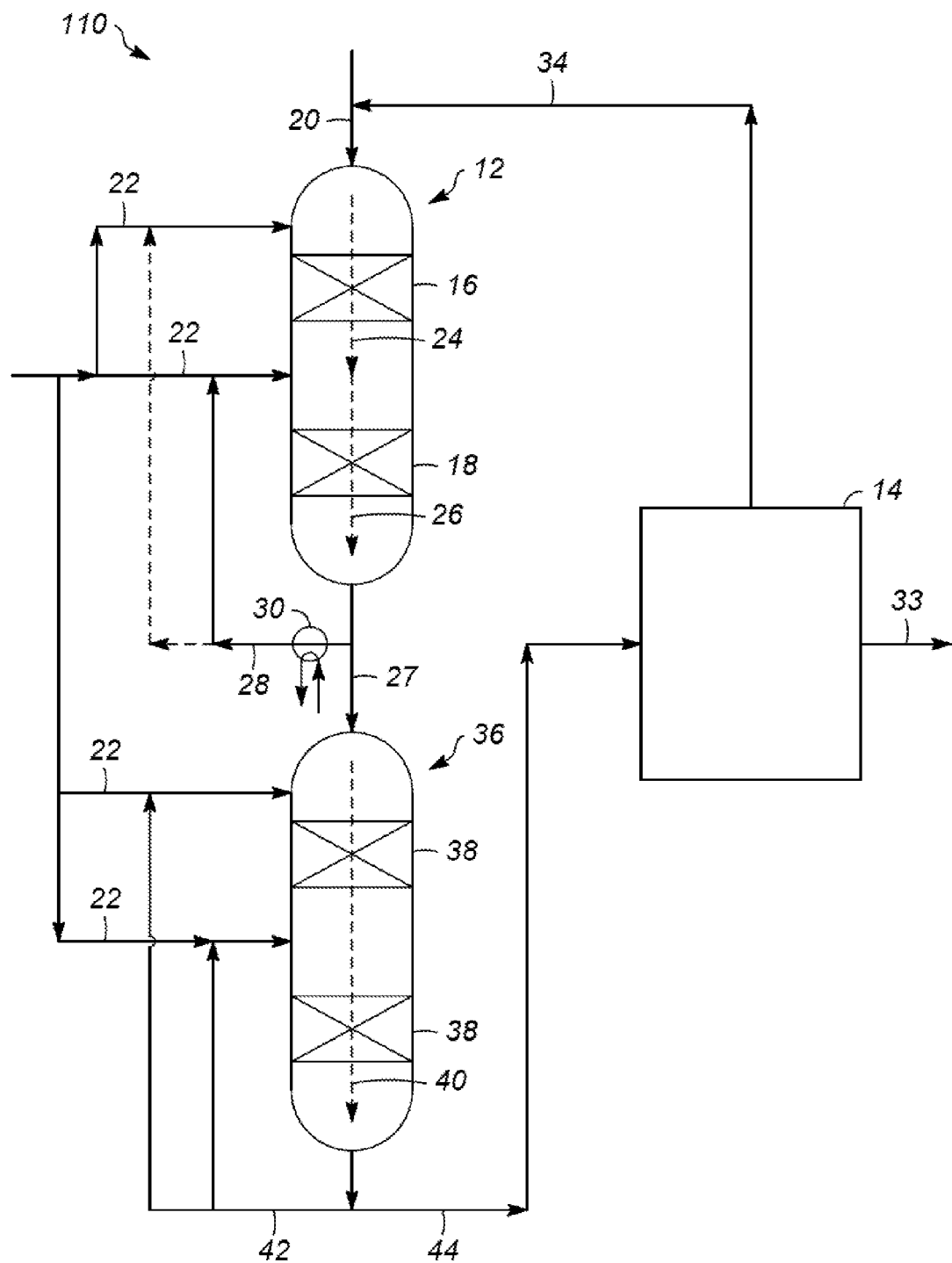
FIG. 2 is a schematic diagram of an alkylation apparatus using another exemplary embodiment of a process for preparing alkylated aromatic compounds.

Another exemplary process will now be described with reference to another alkylation apparatus 110 as shown in FIG. 2. Referring to FIG. 2, the alkylation apparatus 110 includes a multi-bed alkylation reactor 12, a second alkylation reactor 36 in series with the multi-bed alkylation reactor 12, and a separating system 14. The multi-bed alkylation reactor 12 may be the same as described above in the context of FIG. 1. The second alkylation reactor 36 may be identical to the multi-bed alkylation reactor 12, although it is to be appreciated that the second alkylation reactor 36 may include one or more additional alkylation catalyst beds 38 that include a third alkylation catalyst, which may be the same or different from the first alkylation catalyst and the second alkylation catalyst. As shown in FIG. 2, the second alkylation reactor 36 includes two additional downstream alkylation catalyst beds 38, and may include even more such as from 2 to 10 additional downstream alkylation catalyst beds.

When the process is conducted in the alkylation apparatus as shown in FIG. 2, an aromatic compound 20 and an olefin 22 are introduced into the first alkylation catalyst bed 16, the first effluent 24 is produced, the second effluent 26 is produced, and the recycle stream 28 may be recycled to the at least one downstream alkylation catalyst bed 18 and, optionally, the first alkylation catalyst bed 16 as described above in the context of the process conducted in the alkylation apparatus of FIG. 1. However, in this embodiment, the second effluent is split into the recycle stream and an intermediate stream. The recycle stream is recycled to the at least one downstream alkylation reaction and, optionally, the first alkylation reaction as set forth above. The unreacted aromatic compound from the intermediate stream and additional olefin is reacted in at least one additional downstream alkylation reaction in the presence of the third alkylation catalyst to produce a third effluent that includes the alkylated aromatic compound. In particular, as shown in FIG. 2, an intermediate stream 27 is introduced into the second alkylation reactor 36 instead of immediately separating in the separating system 14. The intermediate stream 27 may be introduced into the second alkylation reactor 36 under alkylation conditions to produce a third effluent 40 that includes the alkylated aromatic compound.

The third effluent may be split into a second recycle stream and a product-rich stream. For example, as shown in FIG. 2, the third effluent 40 is split into a second recycle stream 42 and a product-rich stream 44, with the second recycle stream 42 recycled to the at least one additional downstream alkylation catalyst bed 38 of the second alkylation reactor 36. The second recycle stream may be recycled to the at least one additional downstream alkylation reaction, although there are no restrictions on ratios of the second recycle stream to total mass flow in the at least one additional downstream alkylation reactions because fresh aromatic compounds are not introduced into the additional downstream alkylation reactions. The product-rich stream may be separated as described above to produce the alkylated aromatic compound 33 and a return stream 34, although it is to be appreciated that the product-rich stream may alternatively be introduced into yet further alkylation reactions before separation.

Alkylated aromatic products are generally present in the third effluent in greater concentrations than in earlier effluents, due to the late stage of reaction. In an embodiment, the second recycle stream is only recycled to the at least one additional downstream alkylation reaction, and the second recycle stream is not recycled to the first alkylation reaction or to the at least one downstream alkylation reaction that produces the second effluent. As such, in this embodiment the alkylated aromatic compounds that may be present in the second recycle stream in greater concentration than in earlier effluents are not subject to additional reactions that could give rise to further alkylation and produce unwanted dialkyl- and/or trialkyl-aromatic products. For example, as shown in FIG. 2, the second recycle stream 42 is recycled only to the at least one additional downstream alkylation catalyst bed 38, and may be recycled to each additional downstream alkylation catalyst bed 38 in equal or unequal amounts. The second recycle stream 42 is not recycled to any alkylation catalyst beds 16, 18 in the multi-bed alkylation reactor 12 that is upstream of the second alkylation reactor 36.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for preparing alkylated aromatic compounds, the process comprising the steps of:

reacting an aromatic compound and an olefin in a first alkylation reaction in the presence of a first alkylation catalyst to produce a first effluent comprising an alkylated aromatic compound and an unreacted aromatic compound;

reacting the unreacted aromatic compound from the first effluent and additional olefin in at least one downstream alkylation reaction in the presence of a second alkylation catalyst to produce a second effluent comprising the alkylated aromatic compound, wherein the second effluent comprises the unreacted aromatic compound and is split into the recycle stream and an intermediate stream, wherein the process further comprises the step of reacting the unreacted aromatic compound from the intermediate stream and additional olefin in at least one additional downstream alkylation reaction in the presence of a third alkylation catalyst to produce a third effluent comprising the alkylated aromatic compound;

splitting the third effluent stream into a second recycle stream and a product-rich stream, and wherein the second recycle stream is recycled to the at least one additional downstream alkylation reaction;

recycling a recycle stream including the alkylated aromatic compound from the second effluent to the at least one downstream alkylation reaction and, optionally, the first alkylation reaction, and wherein a ratio of the recycle stream to a total mass flow is greater in the at least one downstream alkylation reaction than in the first alkylation reaction; and wherein the alkylation catalyst comprises a zeolitic molecular sieve selected from the group consisting of Y zeolite, beta zeolite, X zeolite, mordenite, zeolite omega, UZM-8, ZSM-5, PSH-3, MCM-22, MCM-36, MCM-49, MCM-56 and mixtures thereof.

2. The process of claim 1, wherein the second effluent is split into the recycle stream and a product-rich stream and wherein the process further comprises separating the product-rich stream to recover the alkylated aromatic compound therefrom.

3. The process of claim 1, wherein reacting the unreacted aromatic compound from the first effluent and the additional olefin in the at least one downstream alkylation reaction is further defined as reacting the unreacted aromatic compound from the first effluent and the additional olefin in at least two downstream alkylation reactions to produce the second effluent.

4. The process of claim 1, wherein the second recycle stream is only recycled to the at least one additional downstream alkylation reaction.

5. The process of claim 1, wherein the aromatic compound and the olefin are reacted in the first alkylation reaction in the absence of the recycle stream.

6. The process of claim 1, wherein the aromatic compound and the olefin are reacted with a temperature rise between alkylation reactions of less than or equal to about 50° C.

7. The process of claim 1, wherein the recycle stream is recycled with the ratio of the recycle stream to the total mass flow being at least 2 times greater in the at least one downstream alkylation reaction than in the first alkylation reaction.

8. The process of claim 7, wherein the recycle stream is recycled with the ratio of the recycle stream to the total mass flow in the first alkylation reaction is less than or equal to 0.5:1.

9. The process of claim 7, wherein the recycle stream is recycled with the ratio of the recycle stream to the total mass flow in the at least one downstream alkylation reaction being greater than or equal to about 1:1.

10. The process of claim 1, wherein reacting the aromatic compound and the olefin in the first alkylation reaction is further defined as reacting benzene and propylene to produce the first effluent comprising cumene.

11. The process of claim 1, wherein reacting the aromatic compound and the olefin in the first alkylation reaction is further defined as reacting benzene and ethylene to produce the first effluent comprising ethylbenzene.

12. The process of claim 1, further comprising the step of cooling the recycle stream prior to recycling to the at least one downstream alkylation reaction and, optionally, the first alkylation reaction.

* * * * *